United States Patent [19]

Asaoka

[11] Patent Number: 5,601,807
[45] Date of Patent: Feb. 11, 1997

[54] CERAMIC TYPE SUNSCREENS

[76] Inventor: Hisatoshi Asaoka, Hamauracho 2-46-9, Niigata 95I, Japan

[21] Appl. No.: 445,377

[22] Filed: May 19, 1995

[51] Int. Cl.$^6$ .................................................. A61K 7/42
[52] U.S. Cl. ........................... 424/59; 106/436; 106/456; 106/481; 423/277; 423/325; 423/598; 423/632; 424/400; 424/401
[58] Field of Search ........................... 424/59, 400, 401; 106/436, 456, 481; 423/277, 325, 598, 632

[56] References Cited

U.S. PATENT DOCUMENTS

| | | | |
|---|---|---|---|
| 4,820,508 | 4/1989 | Wortzman | 424/59 |
| 5,032,390 | 7/1991 | Iwaya et al. | 424/59 |
| 5,064,629 | 11/1991 | Asaoka | 423/279 |
| 5,188,831 | 2/1993 | Nicoll et al. | 424/401 |
| 5,215,580 | 6/1993 | Elfenthal et al. | 106/441 |
| 5,215,749 | 6/1993 | Nicoll et al. | 424/401 |
| 5,234,682 | 8/1993 | Macchio et al. | 424/69 |
| 5,306,486 | 4/1994 | McCook et al. | 424/59 |

FOREIGN PATENT DOCUMENTS 1-257123  10/1989  Japan.
5-286711  11/1993  Japan.

OTHER PUBLICATIONS

Materials Letters, "Formation of titania gels from titanium alkoxide and orthoboric acid in pyridine.I", (pp. 207–212), Feb. 28, 1994, Hisatoshi Asaoka.

Materials Letters, "Sol–gel synthesis of crystalline $ZrO_2$ with partial replacement of zirconium by Al, Nb, Si and Ta.II," (pp. 213–216), Feb. 28, 1994, Hisatoshi Asaoka.

*Crystalline Transformation of Ti–B–O, Al–Ti–B–O, Si–Ti–B–O . . .* , H. Asaoka, 1993 *Journal of Materials Science* pp. 4660–4666.

*Borosilicate synthesis in non–aqueous solvent and its activity for . . .* , H. Asaoka, Mar. 13, 1991 *Journal of Molecular Catalysis* pp. 301–311.

*A New substrate to measure sunscreen protection factors throughout the ultraviolet spectrum*, L. Diffey and J. Robson, May/Jun. 1989, pp. 127–133.

*Primary Examiner*—Shelley A. Dodson
*Attorney, Agent, or Firm*—Sughrue, Mion, Zinn, Macpeak & Seas

[57] ABSTRACT

The invention is directed to provide novel sunscreen materials which are to protect human skin from the harmful ultraviolet radiation. Said sunscreen materials, designated Bolite-S, according to the invention having a composition, expressed in terms of moles of oxides as follows:

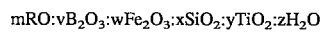

$$mRO:vB_2O_3:wFe_2O_3:xSiO_2:yTiO_2:zH_2O$$

wherein "R" is selected from the group consisting of hydrogen, alkyl groups containing 1–4 carbon atoms, and mixtures thereof, "m" is a value between 0 and about 1200, "v" is a value between 0 and about 500, "w" is a value between 0 and about 100, "x" is a value between 0 and about 200, "y" is a value between 1 and about 300 and "z" is a value of from 0 to about 300, said Bolite-S materials in calcined form having a characteristic X-ray powder diffraction pattern which contains the interplanar spacings and their assigned strengths set forth in Table 1.

2 Claims, 3 Drawing Sheets

CERAMIC TYPE SUNSCREENS

FIELD OF THE INVENTION

The present invention relates to novel sunscreen materials which are to protect human skin from harmful ultraviolet radiation and to methods for their preparation.

BACKGROUND OF THE INVENTION AND RELATED ART STATEMENT

Recent studies have shown that the earth's ozone layer has suffered severe depletion in recent years. Ozone is recognized as the stratospheric component shielding against the harmful forms of ultraviolet (UV) radiation.

In general terms, harmful UV rays, particularly those originating from sunlight, which penetrate the upper atmosphere and reach the earth's surface, can be classified into:

1. the energy-rich UV-B rays (280–320 nm wavelength) which posses an intense physiopathological activity on human skin; these are absorbed just above the dermis and they are responsible for erythema and skin pigmentation, and 2. UV-A rays (320–400 nm wavelength) which penetrate deeper into the skin. The acute and harmful action of the UV-A on the skin is small when compared with that of UV-B, however, the chronic action of UV-A is now considered to be closely related to suntan, aging of the skin and the development of pigmentary blemishes.

Certain organic sunscreens whose molecules absorb the harmful UV rays have been proposed for use in mitigating the deleterious effects of UV radiation. However, these UV ray absorbers involve various problems in safety and the lasting effects thereof. On the other hand, various studies have been carried out on the absorption and scattering of UV rays, and a certain kind of inorganic powder has been known to have a great effect particularly for interrupting UV rays.

In spite of this and other prior proposals, there still exists a need for a highly efficient and thoroughly safe sun protection composition which has a wide spectrum of protection in the harmful UV region.

It is the principal object of the present invention to provide an inorganic oxide suitable for use in sunscreen compositions having improved UV ray-blocking properties. Various inorganic oxides, identified as Bolite compounds, are related art as described in the patent literature and in the published journals. Exemplary of these materials are Bolite-1, -2, -3 and -4 in U.S. Pat. No. 5,064,629, Bolite-7 in J. Mol. Cat. 68, (1991) 301–311 and Bolite-A, -B, -C, -D and -E in Materials Letters, 19 (1994) 213–216 by H. Asaoka. Some of these materials containing titanium are photocatalysts for cleavage of water in their metal-loaded form, but they cannot decompose water under illumination in their metal-unloaded form.

Generally, a superior UV preventing effect is observed in titanium dioxide which is the most potent photocatalyst. The active sunscreening agents must be chemically stable and in particular must be resistant to chemical and photodegradation when on the skin as well as resistant to absorption through the skin. Common titanium dioxide possesses catalytic activity, so that other cosmetic ingredients are liable to degrade.

A cosmetically acceptable sunscreen compound is accompanied by a second necessary component of the compositions such as zinc oxide, tin oxide, iron oxide, silica, mica, octyl methoxycinnamate and green tea as referred to in U.S. Pat. Nos. 4,820,508, 5,032,390, 5,215,749, 5,215,580, 5,234,682 and 5,306,486.

The present invention is concerned with a novel class of inorganic sunscreen materials, hereinafter designated as Bolite-S, having a composition expressed in terms of moles of oxides which may be written as:

$$mRO:vB_2O_3:wFe_2O_3:xSiO_2:yTiO_2:zH_2O$$

wherein "R" is selected from the group consisting of hydrogen, the alkyl groups containing 1–4 carbon atoms, and mixtures thereof, "m" is a value between 0 and about 1200, "v" is a value between 0 and about 500, "w" is a value between 0 and about 100, "x" is a value between 0 and about 200, "y" is a value between 1 and about 300 and "z" is a value of from 0 to about 300.

In accordance with the present invention, the Bolite-S compounds are prepared from the reaction mixtures containing five principal reactants; namely, titanium(IV) alkoxide, iron(III) alkoxide, silicon(IV) alkoxide, orthoboric acid ($H_3BO_3$) and pyridine.

The reaction mechanism for the formation of the Bolite materials from titanium(IV) alkoxide and $H_3BO_3$ in pyridine is described by H. Asaoka in Materials Letters, 19 (1994) 207–212 and 213–216.

The reaction is described as follows:

$$(OR)_3Ti{-}OR + HO{-}B(OH)_2 \rightarrow (OR)_3Ti{-}OH + RO{-}B(OH)_2 \quad (1)$$

$$(OR)_3Ti{-}OH + RO{-}Ti(OR)_3 \rightarrow (OR)_3 + TiO{-}Ti(OR)_3 ROH \quad (2)$$

$$ROH + RO{-}B(OH)_2 + \text{pyridine} \rightarrow HPy^+[(RO)_2B(OH)_2] \quad (3)$$

wherein R is an alkyl group and $HPy^+$ is protonated pyridine.

The reaction (1) in this system involves a transfer of an alkyl group from the alkoxide to orthoboric acid. The reaction (2) can be proceeded by the reactive precursors resulting from the first step of the reaction (1). The reaction (3) take place rapidly so that it is hard to detect alcohol in the reaction medium. The subsequent condensation reactions are possible to occur between the dimer resulting from the reaction (2) and a reactive species resulting from the reaction according to the equation (1).

The reaction can be written as follows:

$$(OR)_3Ti{-}O{-}Ti(OR)_3 + HO{-}Ti(OR)_3 \rightarrow (OR)_3Ti{-}O{-}Ti(OR)_2{-}O{-}Ti(OR)_3 + ROH$$

The successive reactions relating to the above reaction can be applied to all linear polymers.

In reality, the polymerization occurs simultaneously in two and three dimensions. In these cases, the branched unit will be introduced where the molar ratio of $[H_3BO_3]/[\text{alkoxide}]$ is greater than 1.

The prerequisite with respect to the solvent is a sufficient solubility of the alkoxide monomers and the reaction intermediates. Pyridine is a good solvent for metal alkoxides, oligomeric metal oxides and the pyridinium dialkoxydihydroxyborate (1-) complex $(HPy^+[(OR)_2B(OH)_2]^-)$.

The method just described for preparing the monolithic gels can be adapted to the polymerization reaction of plural metal alkoxides in the presence of orthoboric acid in pyridine to produce the multicomponent inorganic compounds.

SUMMARY OF THE INVENTION

The present invention relates to novel sunscreen materials, designated as Bolite-S, and to methods for their preparation. The synthetic Bolite-S materials can generally be represented in terms of moles of oxides, by the formula:

$$mRO:vB_2O_3:wFe_2O_3:xSiO_2:yTiO_2:zH_2O$$

wherein "R" is selected from the group consisting of hydrogen, the alkyl groups containing 1–4 carbon atoms, and mixtures thereof, "m" is a value between 0 and about 1200, "v" is a value between 0 and about 500, "w" is a value between 0 and about 100, "x" is a value between 0 and about 200, "y" is a value between 1 and about 300 and "z" is a value of from 0 to about 300, said Bolite-S materials in calcined form having a characteristic X-ray powder diffraction pattern comprising the interplanar spacings and their assigned strengths set forth in Table 1.

Broadly, a preparing method for the Bolite-S materials and said materials in calcined form comprises:
(a) providing a reaction mixture comprising:
  (1) alkoxides of $Fe(OR)_3$, $Si(OR)_4$ and $Ti(OR)_4$ wherein R is at least one alkyl group selected from the group consisting of methyl, ethyl, propyl, isopropyl, butyl and isobutyl,
  (2) orthoboric acid,
  (3) pyridine as a solvent thereof; and
(b) maintaining said reaction mixture in (a) at suitable reaction conditions to effect formation of gelatinous product, said reaction conditions comprising a reaction temperature ranging from about 10° C. to 110° C., and for a period of from one day to about 30 days; and
(c) removing the mother liquor by centrifugation or filtration from said gelatinous product in (b) and thereafter washing said gelatinous material with water, acetone, methanol, ethanol, propanol, butanol, pyridine, or mixtures thereof; and
(d) drying said washed gelatinous material in (c) at a temperature ranging from about 30° C. to about 400° C. for a time of from one hour to about 72 hours; and
(e) calcining the resulting solid material in (d) in air at a temperature between 400° C. and about 1300° C. for a time of from one hour to about 24 hours.

The Bolite-S sunscreen materials and said materials in calcined form are new and improved products for protection from solar radiation in the wavelength range from 200 to 400 nanometers.

DETAILED DESCRIPTION OF PREFERRED EMBODIMENTS

In order that the synthetic sunscreen materials, designated as Bolite-S, according to the present invention may be obtained, the preparation procedure specified hereinafter can be adopted with advantage.

The Bolite-S materials of the invention are prepared by the reaction of the following reactants; $Fe(OR)_3$, $Si(OR)_4$, $Ti(OR)_4$, and $H_3BO_3$: wherein R in the chemical formula denotes an alkyl group selected from the group consisting of methyl, ethyl, propyl, isopropyl, butyl and isobutyl.

The reactants are dissolved in pyridine in a concentration of from 5% to 30% by weight, preferably about 15% by weight. A technique involves the addition of $H_3BO_3$ to a well stirred solution of said alkoxides in pyridine. The reaction mixture is maintained with stirring at a temperature of from about 10° C. to 110° C., preferably 50° C. to 80° C. in the closed vessel for a period of from one day to about 30 days, preferably for about 7 days, in order to aid a sufficient gelation. The procedure described above is essentially the same as that utilized in the preparation of the materials of Bolite-1, -2, -3 and -4 as described in the aforesaid U.S. Pat. No. 5,064,629.

In this invention, the resulting gel polymer during its preparation is separated from the mother liquor by decantation, centrifugation or filtration and washed with water, acetone, methanol, ethanol, propanol, butanol, pyridine or mixtures thereof, to remove the borate complex (i.e., $HPy^+$ $[(RO)_2B(OH)_2]^-$) resulting from the reaction. The differences in the products obtaining by washing with water and with solvent are for the most part explained by both the amount and distribution of non-condensed —OR and —OH groups in the dried gel. The gels obtained by washing with water contain relatively larger amounts of the —OH groups due to the hydrolysis of the —OR groups. The —OR groups are relatively strongly held at the silicon moiety (e.g., —Si(OR)$_2$—) of the Bolite-S composition. The R of the —OR groups in the gel material can be determined by the combustion method.

The percent carbon in the sample can be determined by oxidizing a weighed sample by heating in oxygen, collecting and weighing the liberated carbon dioxide. The amounts of carbon in the dried gels were found to be in the range of about 0.01% to about 45% by weight. From the carbon content of a given product, the quantity of alkyl groups present in the sample can be calculated. For example, one gram of carbon corresponds to 0.0417 mole of ethyl group and 0.0278 mole of propyl group.

The foregoing dried gel, i.e., the Bolite-S material, is obtained from a wet gel by heating at a temperature ranging from about 30° C. to about 400° C., preferably 40° C. to 120° C. to a constant weight for a time of from one hour to about 72 hours. The amounts of boron in the dried gels are found to be significantly affected by washing of the wet gels with water or solvent. The amount of boron incorporated can be as low as about 0.01% by weight or less depending on the quantity of the washings utilized herein. Without being limited by any theoretical considerations, it is contemplated that boron is actually present in the final Bolite-S products in an oxidized state, such as $B_2O_3$. The amounts of titanium, iron and silicon in the products are found, semiquantitatively, to be proportional to the initial composition of the starting mixture of the alkoxides.

The mole ratios of the various reactants can be varied considerably to produce the Bolite-S materials. In particular, the mole ratios of the initial reactant concentrations for producing the Bolite-S composition can vary as indicated below:

| Mole Ratio Of Initial Reactants | | |
| --- | --- | --- |
| Reactants | Broad | Preferred |
| $Ti(OR)_4/Si(OR)_4$ | 0.005–1500 | 0.01–150 |
| $Si(OR)_4/Fe(OR)_3$ | 0.01–2000 | 0.1–500 |
| $Fe(OR)_3/Ti(OR)_4$ | 0.001–100 | 0.01–50 |
| $H_3BO_3/(Fe(OR)_3 + Si(OR)_4 + Ti(OR)_4)$ | 0.8–6 | 1–3 |

Wherein R represents the alkyl groups, which preferably contain 1 to 4 carbon atoms.

In the aforesaid procedure, it is of particular advantage that the Bolite-S material obtained at substantially lower temperatures of from 30° C. to 120° C. can be used for the purpose of the present invention. High drying temperatures are not necessary for the Bolite-S compounds to be used according to this invention. The products of common titanium dioxide pigment and $TiO_2$—$SiO_2$ glasses are formed from the melt, but this method seems of less economic interest because of the required high temperature and the necessity of transforming the melt into finely-dispersed products.

In a typical preparation of the Bolite-S material of the present invention, the dried gels are soft and can be easily ground to dust fineness, e.g., to about 0.01 μm in particle size. In order to improve the texture of cosmetics using these inorganic powders while taking advantage of their UV preventive effect, the form of the inorganic powder having a fine grain size is an advantage.

Furthermore, for the purpose of improving the affinity for the cosmetic base, the surfaces of the particles are often processed with oil to make them lipophilic. Because titanium dioxide has a high surface activity, it tends to coagulate and has poor spreading quality. Some improvements in this connection are obtained by treatment of titanium dioxide with silicone oils, metal soaps and, particularly, silicone surfactants and the like, as described in U.S. Pat. No. 5,188,831.

The Bolite-S materials according to the invention having functional groups, such as lipophilic —OR groups or hydrophilic —OH groups or combinations thereof, may be used to advantage as an ingredient of cosmetics and skin care products for protection against the sun. Thus the Bolite-S sunscreen materials should be available in a water-dispersible form or in an oil-dispersible form or in both forms.

On heating, the dried gels of the present preparation are converted to ceramics at high temperatures by a sintering process. These ceramic materials are excellent in regard to safety, stability and water-insoluble character and are also useful as a sunscreen. Said ceramic material has a characteristic X-ray powder diffraction pattern which can be employed to identify the Bolite-S material.

Some variations in the X-ray diffraction pattern can occur depending on the mole ratios of the oxides of iron, silicon and titanium in the sample, as well as if the material had been subjected to thermal treatment. The compounds of Bolite-1, -2, -3 and -4 are shown to be isomorphous by the X-ray diffraction patterns as described in J. Mater. Sci., 28 (1993) 4660–4666 by H. Asaoka. They are a crystalline series of $TiO_2$ with partial replacement of titanium by other elements such as aluminum, silicon and the like.

The X-ray investigations of the calcined powder according to this invention were conducted using Ni-filtered Cu—K a radiation. Interplanar spacings are represented by "d" and are expressed in terms of Angstrom units(Å). Relative intensities were calculated from the relation $I/I_0 \times 100$, where $I_0$ is the intensity of the strongest line and I is the intensity of each peak height measured. The relative intensities are arbitrarily assigned the following values:

| Relative Peak Height | Assigned Strength |
|---|---|
| greater than 80 | vs (very strong) |
| 79–40 | s (strong) |
| 39–20 | m (medium) |
| 19–10 | w (weak) |
| less than 9 | vw (very weak) |

These assigned strengths are used throughout this application.

The Bolite-S materials which are X-ray amorphous of this invention do not cause a photocatalytic reaction under illumination.

Inorganic sunscreens such as titanium dioxide and zinc oxide are particularly prone to a "whitening" effect. Whitening detracts from a product's aesthetics. Consumers desire their cosmetics to be unobtrusive, i.e., invisible or skin color. The color of the sunscreen compounds of the present invention will range from white to red-brown depending upon the amount of iron oxide in the compound.

For topical application, sunscreen compositions must be non-toxic and non-irritating to the skin tissue and capable of application to the skin as a uniform continuous film. The monolithic composition of the present invention contains oxides of titanium, iron and silicon as its essential ingredients disposed in pharmaceutically acceptable agents for application to the skin. In a particular embodiment of the present invention, the Bolite-S composition in its calcined form (i.e., ceramic) is available for topical application to human skin with superior safety and exceptional UV ray-blocking properties.

The method for spectrophotometric determination of the compositions of the invention involves spectrophotometric scanning of the tightly packed plane surface (3.0 cm$^2$) of the sample between 200 nm and 900 nm utilizing an Hitachi U-3200 double beam spectrophotometer equipped with a 151-0300 60φ reflection detection system. The control spectrum with magnesium oxide is used to provide the spectral transmittance (% T) of the test sample of the sunscreen material and this transmittance is converted to reflectance (% R).

Both the Bolite-S composition of this invention and said composition in its calcined form display a remarkable increasing reflectance in the wavelength region from 200 nm to 400 nm (the UV-A region and UV-B region).

The invitro Sun Protective Factor (SPF) may be calculated from the transmission measurements as described by Diffey et al., in J. Soc. Cosmet. Chem., 40 (1989) 127–133.

Figure 1:
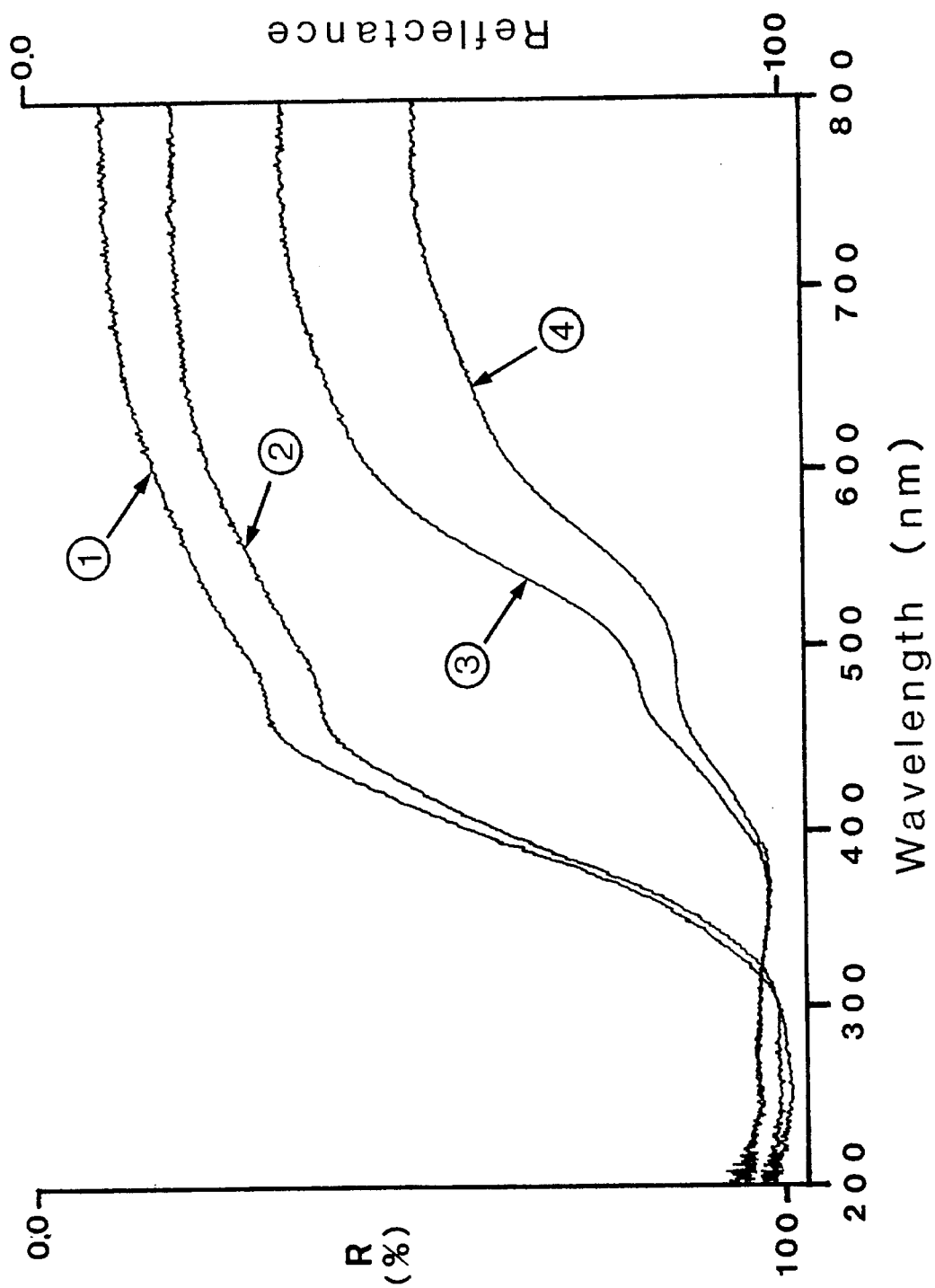
FIG. 1 is a graph showing the reflectance (% R) of the Bolite-S material according to this invention and said material calcined at 900° C. for 5 hours in Example 1 exposed to rays having wavelengths from 200 nm to 800 nm.

The Bolite-S materials of the present invention can be characterized by the X-ray diffraction pattern comprising the significant interplanar spacings and their assigned strengths are summarized from the Table II, III, IV, V, VI and VII, hereinafter. The summarized result is shown in Table I hereinbelow:

TABLE I

| Interplanar Spacing, d(Å) | Assigned Strength |
|---|---|
| 4.89 ± 0.04 | w–vw |
| 4.09 ± 0.04 | m–vw |
| 3.47 ± 0.02 | m–vw |
| 3.24 ± 0.02 | vs |
| 2.75 ± 0.02 | m–vw |
| 2.49 ± 0.02 | s |
| 2.45 ± 0.02 | vw |
| 2.40 ± 0.02 | vw |
| 2.18 ± 0.02 | m |

TABLE I-continued

| Interplanar Spacing, d(Å) | Assigned Strength |
| --- | --- |
| 2.05 ± 0.02 | vw |
| 1.97 ± 0.02 | vw |
| 1.85 ± 0.02 | vw |
| 1.68 ± 0.02 | s |
| 1.62 ± 0.02 | m–w |
| 1.54 ± 0.02 | vw |
| 1.48 ± 0.02 | w–vw |
| 1.35 ± 0.02 | m–w |
| 1.34 ± 0.02 | w–vw |

In the following Tables, the X-ray diffraction patterns of the calcined Bolite-S materials comprise the interplanar spacings and their assigned strengths shown therein depending upon the actual X-ray diffraction analysis.

The following examples demonstrate, but are in no way intended to limit the present invention.

EXAMPLE 1

A sample of Bolite-S material according to this invention was prepared by reacting 9.72 grams of titanium tetraethoxide ($Ti(OC_2H_5)_4$), 5.18 grams of silicon tetraethoxide ($Si(OC_2H_5)_4$), 0.83 grams of iron triisopropoxide ($Fe(O-i-C_3H_7)_3$) and 5.27 grams of $H_3BO_3$ in 200 grams of pyridene.

The reaction mixture was maintained at 70° C. with stirring for 7 days and thereafter cooled to room temperature. The resulting gelatinous product in half of the reaction mixture was separated from the mother liquor by ultrafiltration, thoroughly washed with water and dried at 90° C. to a constant weight. The residual gelatinous product in the remainder of the reaction mixture was separated from the mother liquor by centrifugation and the cake was slurried in acetone and centrifugation was effected once more. Said washing run was repeated four times and thereafter dried at 40° C. for about 48 hours to a constant weight. One gram of each of the resulting dried gels just described was thoroughly blended with 0.2 grams of catalyst (Pt-powder), placed in a platinum boat and thereafter heated under a temperature control program at a temperature of 600° C. in a stream of oxygen, by using an apparatus of the elemental analysis. Evolved $CO_2$ was completely converted into $CaCO_3$.

Combustion analysis of the dried gels showed that the amounts of carbon in the samples were found to be 1.52% by weight when the gel was washed with water and 36.9% by weight when the gel was washed with acetone.

Each of the obtained dried gels, designated as the Bolite-S material, of this Example was calcined in air at 900° C. for 5 hours. The calcined product had the following molar ratios of main ingredients:

$TiO_2/SiO_2$ . . . 1.71

$SiO_2/Fe_2O_3$ . . . 14.0

$Fe_2O_3/TiO_2$ . . . 0.0416

Said ingredients are supplied by suitable source materials (i.e., alkoxides) similar to those previously described.

After calcination, both of the foregoing gels washed with water and with acetone had substantially the same X-ray powder diffraction pattern. The results are presented in Table II and Table III, respectively:

TABLE II

| Interplanar Spacing, d(Å) | Assigned Strength |
| --- | --- |
| 4.87 | vw |
| 4.07 | m |
| 3.47 | vw |
| 3.25 | vs |
| 2.75 | vw |
| 2.48 | s |
| 2.45 | vw |
| 2.39 | vw |
| 2.18 | m |
| 2.05 | vw |
| 1.97 | vw |
| 1.85 | vw |
| 1.68 | s |
| 1.62 | m |
| 1.54 | vw |
| 1.48 | vw |
| 1.35 | m |
| 1.34 | w |

TABLE III

| Interplanar Spacing, d(Å) | Assigned Strength |
| --- | --- |
| 4.89 | vw |
| 4.08 | vw |
| 3.49 | w |
| 3.25 | vs |
| 2.74 | vw |
| 2.49 | s |
| 2.44 | vw |
| 2.40 | vw |
| 2.18 | m |
| 2.05 | vw |
| 1.97 | vw |
| 1.85 | vw |
| 1.68 | s |
| 1.62 | w |
| 1.54 | vw |
| 1.48 | vw |
| 1.36 | w |
| 1.34 | w |

The optical reflectance data of the Bolite-S material according to this Example and said material calcined at 900° C. for 5 hours are shown in FIG. 1. In FIG. 1, the reference numeral ① denotes the spectrum of a sample of the Bolite-S material according to this Example which was obtained by water washing, ② the spectrum of a sample of said Bolite-S material obtained by acetone washing, ③ the spectrum of a calcined sample of said Bolite-S material obtained by water washing and ④ the spectrum of a calcined sample of said Bolite-S material obtained by acetone washing.

The figure shows that both the Bolite-S material according to this Example and said material in calcined form used in these measurements have remarkably increased reflection near the wavelength at 400 nm. A protective covering is a range of UV-A and UV-B.

EXAMPLE 2

In another example of the invention, 10.8 grams of titanium tetraisopropoxide ($Ti(O-i-C_3H_7)_4$), 3.97 grams of $Si(OC_2H_5)_4$, 1.48 grams of $Fe(O-i-C_3H_7)_3$ and 4.71 grams of $H_3BO_3$ were dissolved in 200 grams of pyridine. The procedure and the treatment of the products were performed in the same manner as that described in Example 1 hereinabove.

From the combustion analysis of the resulting dried gels from this Example, the amounts of caren in the samples were found to be 1.81% by weight when the gel was washed with water and 41.1% by weight when the gel was washed with methanol.

Each of the obtained dried gels, designated as Bolite-S material, of this Example was calcined in air at 900° C. for 5 hours. The calcined product had the following molar ratios of main ingredients:

$TiO_2/SiO_2$ ... 2.0

$SiO_2/Fe_2O_3$ ... 6.0

$Fe_2O_3/TiO_2$ ... 0.083

After calcination, both of the gels washed with water and with methanol had substantially the same X-ray powder diffraction pattern. The results are shown in Table IV and V, respectively:

TABLE IV

| Interplanar Spacing, d(Å) | Assigned Strength |
|---|---|
| 4.89 | vw |
| 4.07 | m |
| 3.47 | w |
| 3.25 | vs |
| 2.75 | w |
| 2.48 | s |
| 2.44 | vw |
| 2.39 | vw |
| 2.18 | m |
| 2.05 | vw |
| 1.97 | vw |
| 1.85 | vw |
| 1.68 | s |
| 1.62 | w |
| 1.54 | vw |
| 1.48 | vw |
| 1.35 | w |
| 1.34 | w |

TABLE V

| Interplanar Spacing, d(Å) | Assigned Strength |
|---|---|
| 4.87 | vw |
| 4.07 | vw |
| 3.49 | w |
| 3.25 | vs |
| 2.74 | vw |
| 2.49 | s |
| 2.45 | vw |
| 2.40 | vw |
| 2.18 | m |
| 2.05 | vw |
| 1.97 | vw |
| 1.85 | vw |
| 1.68 | s |
| 1.62 | m |
| 1.54 | vw |
| 1.48 | w |
| 1.36 | m |
| 1.34 | m |

Figure 2:
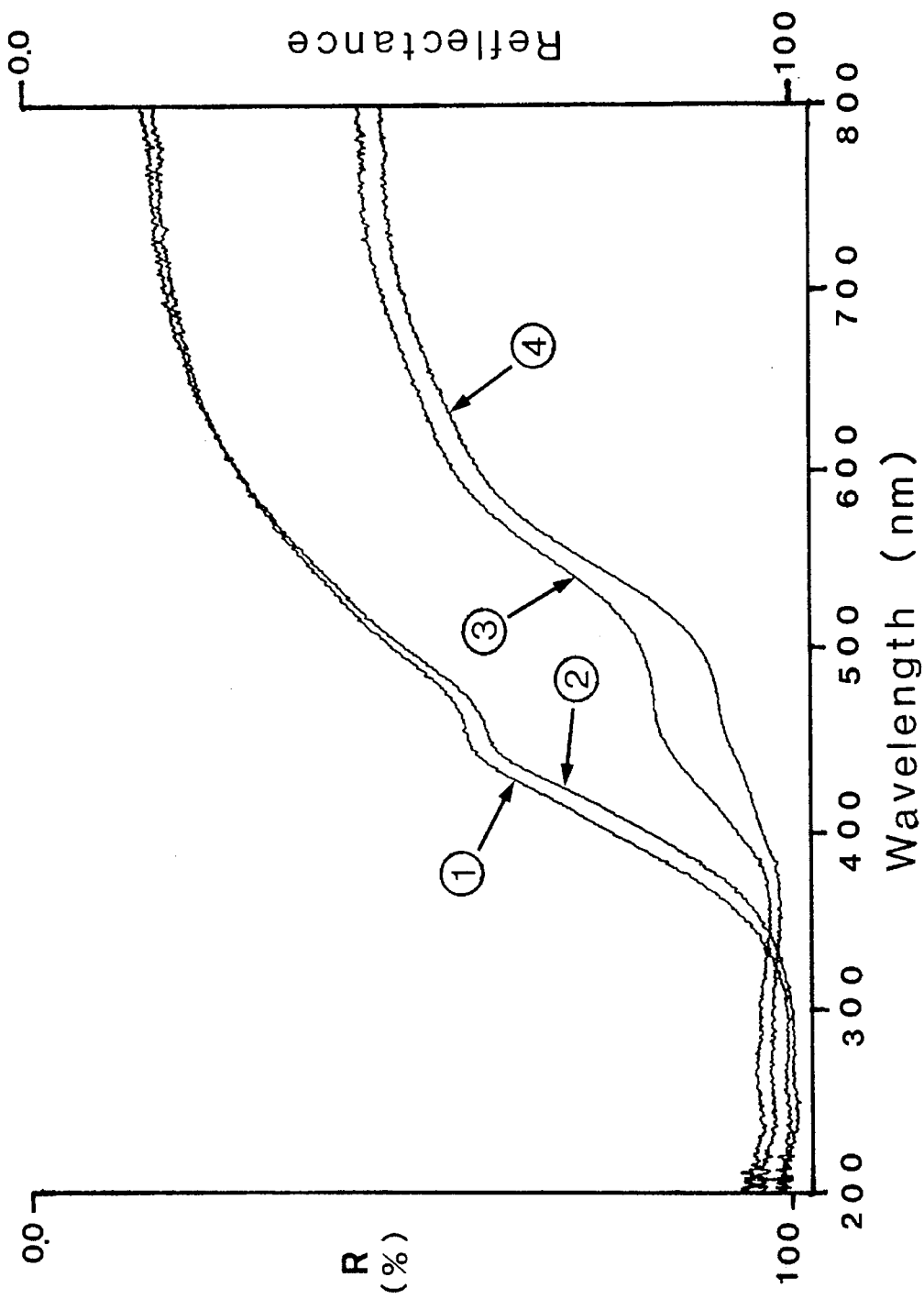
FIG. 2 is a graph showing the reflectance (% R) of the Bolite-S material according to this invention and said material calcined at 900° C. for 5 hours in Example 2 exposed to rays having wavelengths from 200 nm to 800 nm.

The optical reflectance data of the Bolite-S material according to this Example and said material calcined at 900° C. for 5 hours are shown in FIG. 2. In FIG. 2, the reference numeral ① denotes the spectrum of a sample of the Bolite-S material according to this example which was obtained by water washing, ② the spectrum of a sample of said Bolite-S material obtained by methanol washing, ③ the spectrum of a calcined sample of said Bolite-S material obtained by water washing and ④ the spectrum of a calcined sample of said Bolite-S material obtained by methanol washing.

EXAMPLE 3

In another example of the invention, 6.60 grams of $Ti(OC_2H_5)_4$, 7.54 grams of $Si(OC_2H_5)_4$, 1.69 grams of $Fe(O-i-C_3H_7)_3$ and 5.17 grams of $H_3BO_3$ were dissolved in 150 grams of pyridine. The procedure and the treatment of the products were performed in the same manner as that described in Example 1 heretofore.

From the combustion analysis of the resulting dried gels in this Example, the amounts of carbon in the samples were found to be 2.31% by weight when the gel was washed with water and 44.3% by weight when the gel was washed with ethanol.

Each of the obtained dried gels, designated as Bolite-S material, of this Example was calcined at 900° C. in air for 5 hours. The calcined product had the following molar ratios of main ingredients:

$TiO_2/SiO_2$ ... 0.8

$SiO_2/Fe_2O_3$ ... 10.0

$Fe_2O_3/TiO_2$ ... 0.125

After calcination, both of the gels washed with water and with ethanol had substantially the same X-ray powder diffraction pattern. The results are presented in Table VI and VII, respectively:

TABLE VI

| Interplanar Spacing, d(Å) | Assigned Strength |
|---|---|
| 4.89 | w |
| 4.09 | w |
| 3.47 | m |
| 3.24 | vs |
| 2.75 | m |
| 2.49 | s |
| 2.45 | vw |
| 2.40 | vw |
| 2.18 | m |
| 2.05 | vw |
| 1.97 | vw |
| 1.85 | vw |
| 1.68 | s |
| 1.62 | w |
| 1.54 | vw |
| 1.48 | vw |
| 1.35 | m |
| 1.34 | vw |

TABLE VI

| Interplanar Spacing, d(Å) | Assigned Strength |
|---|---|
| 4.89 | vw |
| 4.08 | vw |
| 3.49 | m |
| 3.25 | vs |
| 2.74 | w |
| 2.48 | s |
| 2.45 | vw |
| 2.40 | vw |
| 2.18 | m |
| 2.05 | vw |
| 1.96 | vw |
| 1.86 | vw |
| 1.68 | s |
| 1.62 | w |
| 1.53 | vw |
| 1.48 | w |
| 1.35 | m |
| 1.34 | w |

Figure 3:
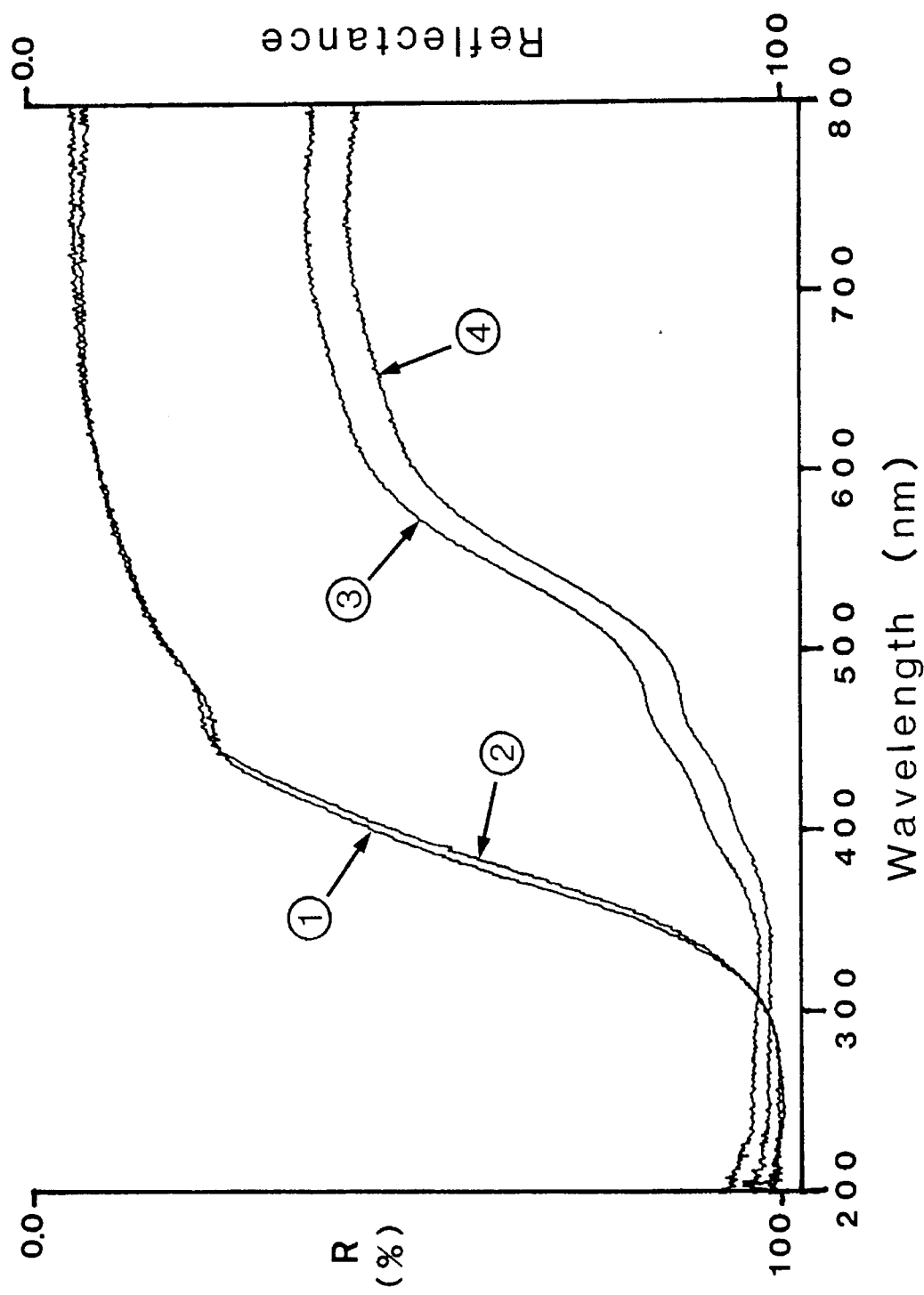
FIG. 3 is a graph showing the reflectance (% R) of the Bolite-S material according to this invention and said material calcined at 900° C. for 5 hours in Example 3 exposed to rays having wavelengths from 200 nm to 800 nm.

The optical reflectance data of the Bolite-S material according to this Example and said material calcined at 900° C. for 5 hours are shown in FIG. 3. In FIG. 3, the reference numeral ① denotes the spectrum of a sample of the Bolite-S material according to this Example which was obtained by water washing, ② the spectrum of a sample of said Bolite-S material obtained by ethanol washing, ③ the spectrum of a calcined sample of said Bolite-S material obtained by water washing and (4) the spectrum of a calcined sample of said Bolite-S material obtained by ethanol washing.

What is claimed is:

1. Synthetic sunscreen materials having a composition expressed in terms of moles of oxides as follows:

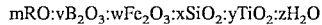

wherein "R" is selected from the group consisting of hydrogen, alkyl groups containing 1–4 carbon atoms, and mixtures thereof, "m" is a value between 0 and about 1200, "v" is a value between 0 and about 500, "w" is a value between 0 and about 100, "x" is a value between 0 and about 200, "y" is a value between 1 and about 300 and "z" is a value of from 0 to about 300, said synthetic sunscreen materials in calcined form having a characteristic X-ray powder diffraction pattern comprising interplanar spacings and corresponding assigned strengths as set forth below:

| Interplanar Spacing, (Å) | Assigned Strength |
|---|---|
| 4.89 ± 0.04 | w–vw |
| 4.09 ± 0.04 | m–vw |
| 3.47 ± 0.02 | m–vw |
| 3.24 ± 0.02 | vs |
| 2.75 ± 0.02 | m–vw |
| 2.49 ± 0.02 | s |
| 2.45 ± 0.02 | vw |
| 2.40 ± 0.02 | vw |
| 2.18 ± 0.02 | m |
| 2.05 ± 0.02 | vw |
| 1.97 ± 0.02 | vw |
| 1.85 ± 0.02 | vw |
| 1.68 ± 0.02 | s |
| 1.62 ± 0.02 | m–w |
| 1.54 ± 0.02 | vw |
| 1.48 ± 0.02 | w–vw |
| 1.35 ± 0.02 | m–w |
| 1.34 ± 0.02 | w–vw. |

2. A method for preparing synthetic sunscreen materials and said synthetic sunscreen materials in calcined form having a composition expressed in terms of moles of oxides as follows:

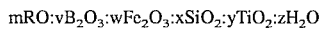

wherein "R" is selected from the group consisting of hydrogen, alkyl groups containing 1–4 carbon atoms, and mixtures thereof, "m" is a value between 0 and about 1200, "v" is a value between 0 and about 500, "w" is a value between 0 and about 100, "x" is a value between 0 and about 200, "y" is a value between 1 and about 300 and "z" is a value of from 0 to about 300, said synthetic sunscreen materials in calcined form having a characteristic X-ray powder diffraction pattern comprising interplanar spacings and corresponding assigned strengths as set forth below:

| Interplanar Spacing, d(Å) | Assigned Strength |
|---|---|
| 4.89 ± 0.04 | w–vw |
| 4.09 ± 0.04 | m–vw |
| 3.47 ± 0.02 | m–vw |
| 3.24 ± 0.02 | vs |
| 2.75 ± 0.02 | m–vw |
| 2.49 ± 0.02 | s |
| 2.45 ± 0.02 | vw |
| 2.40 ± 0.02 | vw |
| 2.18 ± 0.02 | m |
| 2.05 ± 0.02 | vw |
| 1.97 ± 0.02 | vw |
| 1.85 ± 0.02 | vw |
| 1.68 ± 0.02 | s |
| 1.62 ± 0.02 | m–w |
| 1.54 ± 0.02 | vw |
| 1.48 ± 0.02 | w–vw |
| 1.35 ± 0.02 | m–w |
| 1.34 ± 0.02 | w–vw | which method comprises:

(a) providing a reaction mixture comprising:

(1) alkoxides of $Fe(OR)_3$, $Si(OR)_4$ and $Ti(OR)_4$ wherein R is at least one alkyl group selected from the group consisting of methyl, ethyl, propyl, isopropyl, butyl and isobutyl, (2) orthoboric acid, (3) pyridine as a solvent thereof; and (b) maintaining said reaction mixture in (a) at suitable reaction conditions to effect formation of gelatinous product, said reaction conditions comprising a reaction temperature ranging from about 10° C. to 110° C., for a period of from one day to about 30 days; and (c) removing the mother liquor by centrifugation or filtration from said gelatinous product in (b) and thereafter washing said gelatinous material with water, acetone, methanol, ethanol, propanol, butanol, pyridine, or mixtures thereof; and (d) drying said washed gelatinous material in (c) at a temperature ranging from about 30° C. to about 400° C. for a time of from one hour to about 72 hours; and (e) calcining the resulting solid material in (d) in air at a temperature between 400° C. and about 1300° C. for a time of from one hour to about 24 hours.

* * * * *